United States Patent
Aurbach et al.

(10) Patent No.: US 6,316,141 B1
(45) Date of Patent: Nov. 13, 2001

(54) HIGH-ENERGY, RECHARGEABLE, ELECTROCHEMICAL CELLS WITH NON-AQUEOUS ELECTROLYTES

(75) Inventors: Doron Aurbach, Bnei Brak; Yosef Gofer, Hod Hasharon; Alexander Schechter, Neveh Monoson; Lu Zhonghua, Ramat-Gan; Chaim Gizbar, Rishon Lezion, all of (IL)

(73) Assignee: Bar Ilan University, Ramat Gan (IL)

( * ) Notice: Subject to any disclaimer, the term of this patent is extended or adjusted under 35 U.S.C. 154(b) by 0 days.

(21) Appl. No.: 09/419,940

(22) Filed: Oct. 18, 1999

(51) Int. Cl.[7] .................................................. H01M 6/04
(52) U.S. Cl. ........................ 429/199; 429/324; 429/188
(58) Field of Search .................................. 429/324, 199, 429/206, 207, 306, 319, 321, 322, 323, 218.1, 220, 231.5; 423/61; 252/182.1

(56) References Cited

U.S. PATENT DOCUMENTS

| | | | | |
|---|---|---|---|---|
| 4,104,450 | * | 8/1978 | Whitney et al. | 429/194 |
| 4,139,681 | * | 2/1979 | Klemann et al. | 429/191 |
| 4,894,302 | * | 1/1990 | Hoffman et al. | 429/194 |
| 4,917,871 | * | 4/1990 | Dahn et al. | 423/61 |
| 5,491,039 | * | 2/1996 | Shackle | 429/192 |
| 5,849,432 | * | 12/1998 | Angell et al. | 429/190 |

FOREIGN PATENT DOCUMENTS

| | | | | |
|---|---|---|---|---|
| 6-223818 | * | 8/1994 | (JP) | H01M/4/02 |
| 5-343065 | * | 12/1993 | (JP) | H01M/4/58 |

\* cited by examiner

*Primary Examiner*—Stephen Kalafut
*Assistant Examiner*—R. Alejandro
(74) *Attorney, Agent, or Firm*—Mark M. Friedman

(57) ABSTRACT

A non-aqueous electrolyte for use in an electrochemical cell comprising: (a) at least one organic solvent; (b) at least one electrolytically active salt represented by the formula:

$$M^{r+m}(ZR_nX_{q-n})_m$$

in which: M' is selected from a group consisting of magnesium, calcium, aluminum, lithium and sodium; Z is selected from a group consisting of aluminum, boron, phosphorus, antimony and arsenic; R represents radical selected from the following groups: alkyl, alkenyl, aryl, phenyl, benzyl, and amido; X is a halogen (I, Br, Cl, F); m=1–3; and n=0–5 and q=6 in the case of Z=phosphorus, antimony and arsenic, and n=0–3 and q=4 in the case of Z=aluminum and boron. Rechargeable, high energy density electrochemical cells containing an intercalation cathode, a metal anode, and an electrolyte of the above-described type are also disclosed.

19 Claims, 2 Drawing Sheets

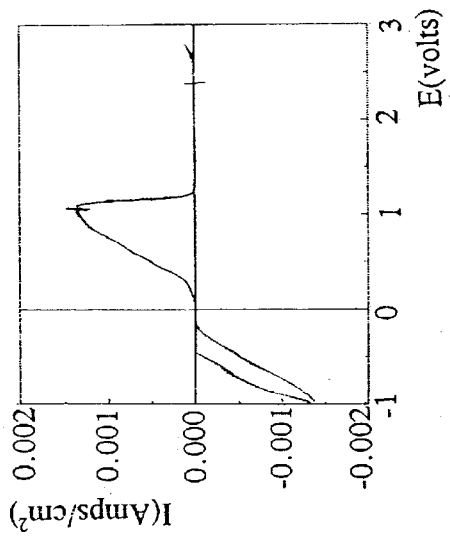
Fig. 1A  (Al-C13-Bu)$_2$-Mg
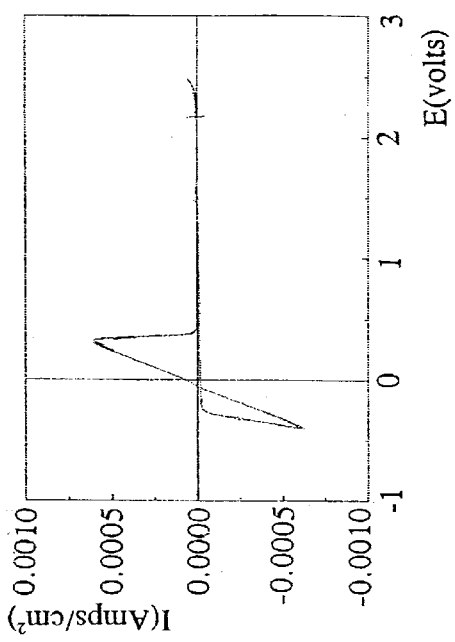
Fig. 1B  (Al-C12-Et-Bu)$_2$-Mg
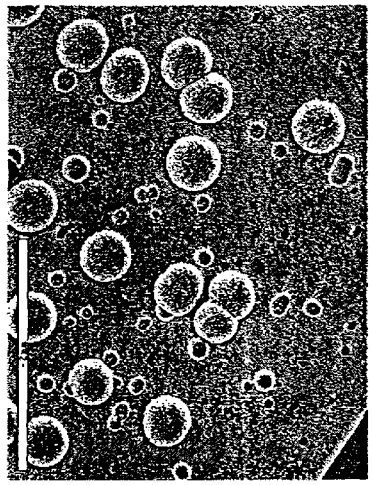
Fig. 2A  DEPOSITION
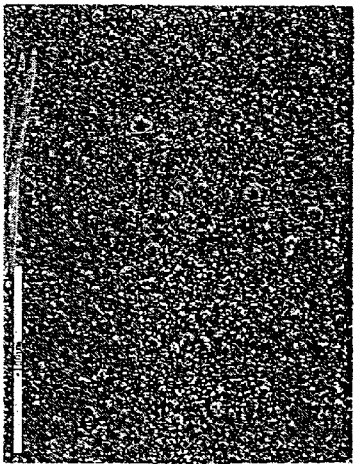
Fig. 2C  DEPOSITION
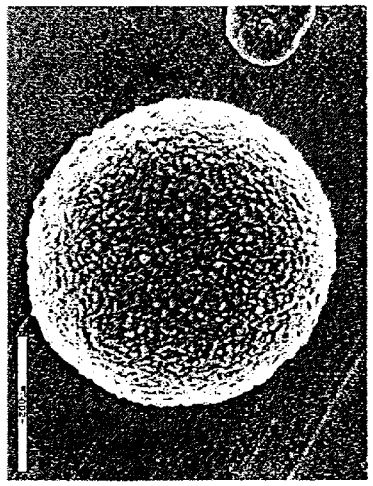
Fig. 2B  ZOOM
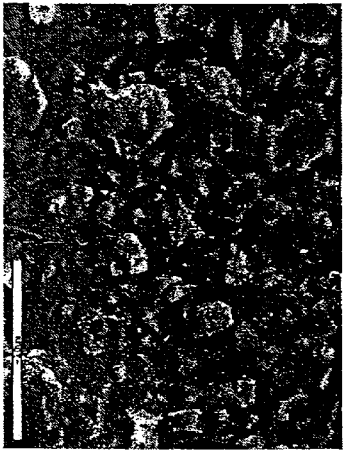
Fig. 2D  ZOOM

HIGH-ENERGY, RECHARGEABLE, ELECTROCHEMICAL CELLS WITH NON-AQUEOUS ELECTROLYTES

FIELD AND BACKGROUND OF THE INVENTION

The present invention relates to electrochemical cells utilizing a non-aqueous liquid electrolyte with an intercalation cathode, and more particularly, to electrochemical cells utilizing a non-aqueous liquid electrolytic solution, an intercalation cathode and a magnesium anode.

Rechargeable, high energy density electrochemical cells of various kinds are known. Such cells usually consist of a transition metal oxide or chalcogenide cathode-active material, an anode-active alkali metal or alkali metal intercalation compound, and an electrolytic solution containing a dissolved alkali-based salt in an aprotic organic or inorganic solvent or polymer.

Theoretically, a rechargeable cell is capable of charging and discharging indefinitely, however, in practice such performance is unattainable. The degradation mechanisms of the various anodes, cathodes and electrolytes are complex and are reviewed in the general literature.

Two basic types of cathodes are appropriate for a battery system that is rechargeable at ambient temperatures. A liquid cathode can be used, allowing reactions to take place with facility. Liquid cathodes are also advantageous in that thin films or crusts forming on the surface of the cathode tend to crack, such that the cathode activity remains high over the course of the cycling. The mobility of the cathodic material is a liability, however, in that contact with the anode short-circuits the cell. Thus, an electrochemical cell with a liquid cathode requires protective, insulating films on the anode.

A solid cathode must be insoluble in the electrolyte, and must be able to receive and release a charge-compensating ion in a substantially reversible and fast manner. A prime example of a solid cathode of this variety is an intercalation cathode. Intercalation chemistry focuses on the insertion of ions or neutral molecules into an inorganic or organic matrix. In a typical intercalation cathode, cations dissolved in the electrolytic solution are inserted into the inorganic matrix structure.

One type of intercalation materials of particular importance is known as Chevrel-phase material, or Chevrel compounds. Chevrel compounds contain an invariant portion consisting of molybdenum and a chalcogen—sulfur, selenium, tellurium, or mixtures thereof. The invariant portion is generally of the formula $Mo_6T_n$, where T represents the chalcogen and n is usually about 8. The unique crystal structure of Chevrel-phase materials allows the insertion of one or more metal ions in a reversible, partially-reversible, or irreversible fashion. The stoichiometry of the intercalation compound can be represented as $M_xMo_6T_n$, where M represents the intercalated metal and x may vary from 0 (no intercalated metal) to 4 or less, depending on the properties of the particular metal.

The intercalation of metal ions into the Chevrel compound releases energy. Since the process is partially or fully reversible, these compounds are particularly suitable as electrodes in electrochemical cells. For example, lithium, the predominant intercalation ion, can be removed from the Chevrel compound by the application of electrical energy. The energy is released as electrical energy upon reintercalation.

The cathode-active material in the high energy density, rechargeable electrochemical cells must be paired with a suitable anode-active material, which is most commonly made of an active metal such as alkali metals. However, the performance of a particular anode-cathode couple is strongly influenced by the nature of the electrolyte system. Certain non-aqueous electrolytes are known to perform well with a particular anode-cathode couple and be ineffective or significantly less effective with other anode-cathode couples, because of reaction between the components causes degradation over time. As a result, much of the prior art relates to the cathode-active material, the anode-active material and the electrolyte not only as independent entities, but also as units within an appropriate battery system.

U.S. Pat. No. 4,104,451 to Klemann et al. discloses reversible batteries with an alkali metal anode, a chalcogenide cathode, and organometallic alkali metal salts in organic solvents as the electrolyte system. Non-aqueous electrolyte systems containing alkali metal salts of organic boron-based or aluminum-based anions are disclosed.

Organoborate salts of alkali metals represented by the formula:

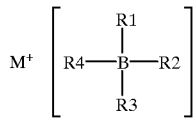

are disclosed in U.S. Pat. No. 4,511,642 to Higashi et al., wherein R1–R4 are organic radicals selected from the following groups: alkyl, aryl, alkenyl, cycloalkyl, allyl, heterocyclic, and cyano, and $M^+$ represents an alkali metal ion.

U.S. Pat. No. 4,139,681 describes cells containing electrolytically active metal salt complexes having the formula $ZMR_nX_i$, wherein Z is a metal from a group containing aluminum, the Rs are specified haloorganic radicals, the Xs are selected from various halides, alkyls, aryls, alkaryls and aralkyls. M is specified to be an alkali metal, with lithium being the preferred embodiment.

U.S. Pat. No. 4,542,081 to Armand et al. describes solutions for the constitution of solid electrolyte materials of electrochemical generators. The compound is of the formula:

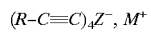

in which Z is a trivalent element capable of entering into 4-coordination, such as aluminum, and R represents groups which are non-proton donors. M is specified to be an alkali metal.

The prior art described above, including U.S. Pat. Nos. 4,104,451, 4,511,642, 4,139,681 and 4,542,081, specifies that M is an alkali metal. The use of an alkaline earth metal anode such as magnesium would appear disadvantageous relative to the use of an alkali metal such as lithium because alkali metal anodes are much more readily ionized than are alkaline earth metal anodes. In addition, on recharge the cell must be capable of re-depositing the anode metal that was dissolved during discharge, in a relatively pure state, and without the formation of deposits on the electrodes.

However, there are numerous disadvantages to alkali batteries. Alkali metals, and lithium in particular, are expensive. Alkali metals are highly reactive. Alkali metals are also highly flammable, and fire due to the reaction of alkali metals with oxygen or other active materials is extremely difficult to extinguish. Lithium is poisonous and compounds thereof are known for their severe physiological effects, even in minute quantities. As a result, the use of alkali metals requires specialized facilities, such as dry rooms, specialized equipment and specialized procedures.

In contradistinction, magnesium metal and aluminum metal are easy to process. The metals are reactive, but undergo rapid passivation of the surface, such that the metals are highly stable. Both magnesium and aluminum are inexpensive relative to the alkali metals.

U.S. Pat. No. 4,894,302 to Hoffman et al. discloses an electrochemical cell having an intercalation cathode, an alkaline earth anode, and a non-aqueous liquid electrolyte containing an organic solvent and an electrolytically active, organometallic alkaline earth metal salt represented by the formula:

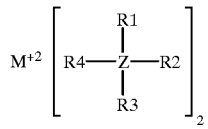

wherein Z is boron or aluminum; R1–R4 are radicals selected from the following groups: alkyl, aryl, alkaryl, aralkyl, alkenyl, cycloalkyl, allyl, heterocyclic alkyl, and cyano; and M represents an alkaline earth metal such as magnesium. The radicals can be inertly substituted with substituents that have no detrimental effect upon the electrolytic properties of the electrolyte composition with respect to effectiveness in an electrochemical cell, such as halogenated or partially halogenated derivatives of the above groups. While exhaustive care is taken to disclose a broad range of organic radicals and halogenated organic radicals, bonding the metallic species of the anion (Z) to another inorganic species is not considered.

U.S. Pat. No. 5,491,039 describes a solid, single-phase electrolyte containing a solid polymeric matrix and an organometallic ion salt represented by the formula:

wherein Z is boron, aluminum or titanium; Rs are various substituted or unsubstituted organic radicals; M is lithium, sodium, potassium, or magnesium, c is 1 or 2, and n is an integer from 1 to 6. As in U.S. Pat. No. 4,894,302, a broad range of organic radicals and halogenated organic ris disclosed, but bonding the metallic species of the anion (Z) to another inorganic species is not reported.

Both U.S. Pat. No. 5,491,039 and U.S. Pat. No. 4,894,302 disclose electrochemical cells having an alkaline earth anode such as magnesium. For commercial application, however, such magnesium batteries must be essentially rechargeable and must have a reasonable shelf life. Sustaining a voltage of 1.5 volts is problematic or impossible with the usual intercalation cathodes and electrolytes according to prior art. Magnesium batteries operating at 1.5 volts are particularly prone to electrolyte decomposition and to encrustation/passivation of both electrode surfaces.

Thus, there is a widely recognized need for, and it would be highly advantageous to have, an improved non-aqueous electrolyte that allows the production of a practical, rechargeable magnesium battery which would be safer and cleaner, and more durable, efficient and economical than heretofore known.

SUMMARY OF THE INVENTION

The present invention is a new type of electrolyte for use in electrochemical cells. The properties of the electrolyte include high conductivity and an electrochemical window that can exceed 2 V vs. Mg/Mg$^{+2}$. The use of the electrolyte in an appropriate cell promotes the substantially-reversible deposition of the intercalating metal.

According to the teachings of the present invention there is provided a non-aqueous electrolyte for use in an electrochemical cell, said electrolyte comprising; (a) at least one organic solvent; (b) at least one electrolytically active salt represented by the formula:

in which: M' is selected from a group consisting of magnesium, calcium, aluminum, lithium and sodium; Z is selected from a group consisting of aluminum, boron, phosphorus, antimony and arsenic; R represents radicals selected from the following groups: alkyl, alkenyl, aryl, phenyl, benzyl, and amido; X is a halogen (I, Br, Cl, F); m=1–3; and n=0–5 and q=6 in the case of Z=phosphorus, antimony and arsenic, and n=0–3 and q=4 in the case of Z=aluminum and boron.

According to further features in preferred embodiments of the invention described below, the electrolyte according to the present invention is incorporated into specific electrochemical cells comprised of said electrolyte and an appropriate anode-cathode pair.

According to further features in the preferred embodiments, one such appropriate anode-cathode pair is a magnesium metal anode and a magnesium insertion-compound cathode.

In yet another preferred embodiment, the magnesium insertion-compound cathode is a magnesium-Chevrel intercalation cathode of the formula:

wherein X=0–1 and y=0–2.

The present invention successfully addresses the shortcomings of the presently-known electrolytes and provides the basis for the production of a viable, rechargeable magnesium battery with a nominal voltage exceeding 1.5 volts.

BRIEF DESCRIPTION OF THE DRAWINGS

The invention is herein described, by way of example only, with reference to the accompanying drawings, wherein:

FIG. 1a and FIG. 1b are graphs displaying typical cyclic voltammograms of magnesium salts solutions in tetrahydrofuran (THF) using a gold electrode;

FIGS. 2a–2d are Scanning Electron Microscope (SEM) micrographs showing different forms of metallic magnesium deposition on a copper electrode.

DESCRIPTION OF THE PREFERRED EMBODIMENTS

Figure 3:
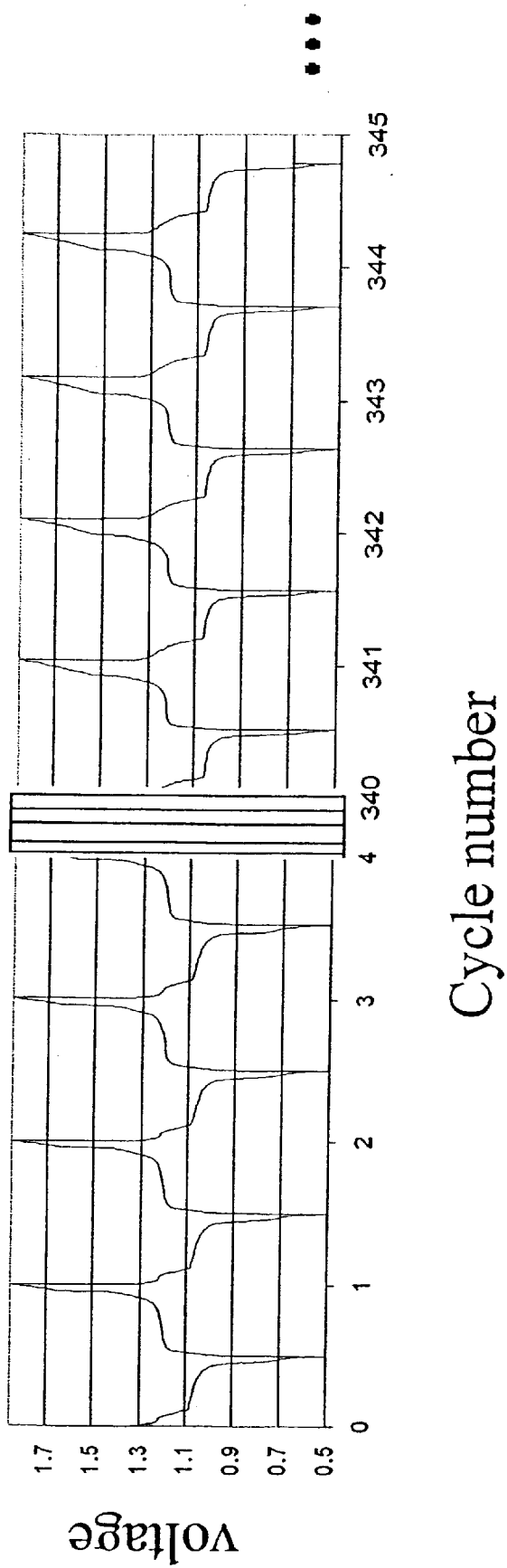
FIG. 3 is a graph of the voltage patterns of an electrochemical cell consisting of a Chevrel-phase cathode, magnesium metal anode, and an electrolyte containing Mg(AlCl$_2$BuEt)$_2$ salt in THF, in which cycles 340–345 are plotted next to the first five cycles (cycles 1–5).

The present invention is a new type of electrolyte for use in electrochemical cells. The properties of the electrolyte include high conductivity and an electrochemical window that can exceed 2 V vs. Mg/Mg$^{+2}$. The use of the electrolyte in an appropriate cell promotes the substantially-reversible deposition of magnesium metal on the anode current collector and the reversible intercalation of magnesium in the cathode material.

Although alkali metals are readily ionized, the use of other metal anodes, such as magnesium or aluminum has decided advantages. Magnesium and aluminum are very inexpensive relative to alkali metals. Alkali metals are highly reactive and highly flammable, and alkali fire is extremely difficult to extinguish. Lithium in particular is poisonous and compounds thereof are known for their severe physiological effects, even in minute quantities. As a result, the use of alkali metals requires specialized facilities, such as dry rooms, specialized equipment and specialized procedures.

Magnesium and aluminum are reactive, but undergo rapid passivation of the surface, such that for all practical purposes, the metals are highly stable. Magnesium and aluminum are available and inexpensive, non-toxic, non-hazardous, and easy to work with, and as such, are highly-desirable raw materials for electrochemical cells and for electrolytic solutions in particular.

Although primary electrochemical cells based on magnesium are known, such cells are non-rechargeable and are used solely for military applications. Sustaining a voltage of 1.5 volts is problematic or impossible with the usual intercalation cathodes and electrolytes according to prior art. Magnesium batteries operating at 1.5 volts are particularly prone to electrolyte decomposition and to encrustation/passivation of the electrode surface.

The present invention provides a non-aqueous electrolyte for use in an electrochemical cell comprising: (a) at least one organic solvent; (b) at least one electrolytically active salt represented by the formula:

$$M^{+m}(ZR_nX_{q-n})_m$$

in which : M' is selected from a group consisting of magnesium, calcium, aluminum, lithium and sodium; Z is selected from a group consisting of aluminum, boron, phosphorus, antimony and arsenic; R represents radical selected from the following groups: alkyl, alkenyl, aryl, phenyl, benzyl, and amido; X is a halogen (I, Br, Cl, F); m=1–3; and n=0–5 and q=6 in the case of Z=phosphorus, antimony and arsenic, and n=0–3 and q=4 in the case of Z=aluminum and boron.

As described above, the electrochemical window of a cell with an electrolyte according to the present invention and an appropriate anode-cathode pair is 2 volts, such that the cell can be operated in a stable, reversible fashion at 1.5 volts without decomposition of the electrolyte and encrustation of the electrodes.

In a preferred embodiment of the invention, the electrolyte according to the present invention functions in an electrochemical cell with a metal anode and an intercalation cathode.

Certain non-aqueous electrolytes are known to perform well with a particular anode-cathode couple and be ineffective or significantly less effective with other anode-cathode couples, either because the electrolyte is not inert or because it degrades during cycling. It is relevant, therefore, to treat the electrolyte, not only as an independent entity, but also as a unit within a system containing an appropriate anode-cathode pair.

Hence, according to further features in preferred embodiments of the invention described below, the electrolyte according to the present invention is incorporated into specific electrochemical cells containing an appropriate anode-cathode pair.

While various metals are suitable as anodes for the electrolytic solution, including magnesium, lithium, aluminum and calcium, a particularly preferred of a battery according to the present invention includes the electrolyte according to the present invention, a magnesium metal anode and a magnesium insertion compound cathode.

In yet another preferred embodiment, the magnesium insertion-compound cathode is a magnesium-Chevrel intercalation cathode of the formula:

$$Cu_xMg_yMo_6S_8$$

wherein x=0–1 and y=0–2.

The principles and operation of an electrolytic cell with an improved electrolyte according to the present invention may be better understood with reference to the drawings and the accompanying description.

The electrolyte composition of the present invention includes an organic solvent and electrochemically-active organometallic salts of the formula $M^{+m}(ZR_nX_{q-n})_m$, as described above. Organometallic salts of this form may be combined with compatible non-organometallic salts or with compatible organometallic salts of other forms.

Many different organic solvents are suitable for use in the electrolyte of the present invention, including ethers, organic carbonates, lactones, ketones, nitriles, aliphatic and aromatic hydrocarbon solvents and organic nitro solvents. More specifically, suitable solvents include acetonitrile, hexane, toluene, THF, diglyme, triglyme, tetraglyme, dimethoxyethane, diethoxyethane, diethylether, dimethoxyethane, dimethylsulfoxide, dimethylsulfite, sulfolane, and nitromethane.

Intercalation cathodes used in conjunction with the electrolyte according to the present invention preferably include transition metal oxides, chalcogenides and halogenides and combinations thereof. More preferably, the transition metal oxides may optionally include $V_2O_5$, $TiS_2$, $MoS_2$, $ZrS_2$, $Co_3O_4$, $MnO_2$, $Mn_2O_4$, and the chalcogenides include Chevrel-phase compounds.

EXAMPLE 1

A magnesium-Chevrel intercalation cathode for use in conjunction with the electrolyte according to the present invention was synthesized according to the procedure developed by Goecke, Schölhorn et al. (*Inorg. Chem.* 26, p. 1805 (1987)). Elemental sulfur, molybdenum and copper of high purity were added in a stoichiometric ratio of 4:3:1. After intimate mixing and pressing into pellets, the mixture was sealed in a quartz ampoule under a vacuum of $10^{-5}$ Torr. The ampoule was placed in a furnace, and the temperature was raised at a rate of 400° C./h to 450° C. The temperature was maintained at 450° C. for 24 hours. Again, the temperature was raised at a rate of 400° C./h to 700° C. and was maintained at 700° C. for 24 hours. The temperature was then raised at a rate of 120° C./h to 1050° C. and was maintained at 1050° C. for 48 hours. After cooling to room temperature at a rate of 120° C./h, the ampoule was broken open. The copper molybdenum sulfide ($Cu_2Mo_6S_8$) obtained was milled into fine powder using mortar and pestle.

The copper molybdenum sulfide powder was mixed with Teflon-loaded carbon black (CB). The resulting paste was spread on stainless steel mesh and pressed. The composite electrode formed was dried under vacuum at room temperature for 24 hours.

The electrode was subsequently subjected to electrochemical pretreatment in which some of the copper ions in the host matrix ($Cu_2Mo_6S_8$) were deinserted. The electrochemical deintercalation of copper was performed in a non-aqueous medium, a 1M solution of $Mg(ClO_4)_2$ in acetonitrile. The deinsertion was performed by a galvanostatic charging process in which the upper limit of the potential was controlled.

After thorough washing in acetonitrile and subsequent drying of the electrode, charging-discharging cycles were conducted in a 1M solution of $Mg(ClO_4)_2$ in acetonitrile at various scan rates between −1.6 V and 0.01 V, relative to the $Ag/Ag^{+1}$ reference electrode. A pronounced electrochemical redox activity was observed, with a main oxidation peak at −1.219 V vs. $Ag/Ag^+$ and a corresponding main reduction peak at −1.41 V vs. $Ag/Ag^+$. The charge associated with the intercalation-deintercalation process was 71 mAh/g and 72 mAh/g, respectively, which correspond to y=1.09–1.12 in the formula:

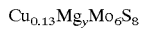

The chemical and electrochemical reversibility of the intercalation process was demonstrated over multiple cycles.

EXAMPLE 2

Referring now to the drawings, FIG. 1a and FIG. 1b are graphs displaying typical cyclic voltammograms of ether-magnesium organo- halo-aluminates solutions in tetrahydrofuran (THF) using a gold electrode.

FIG. 1a shows the potentiodynamic behavior of $Mg(AlCl_3Bu)_2$ obtained with THF solution using a gold working electrode. The peak at −1 V is due to the deposition of magnesium metal, and the peak at around 0.9 V is attributed to the subsequent electrochemical dissolution of the magnesium metal. The electrochemical window obtained with this system exceeds 2.6 V. It is clearly evident from the cyclic voltammogram that the process of magnesium deposition and dissolution is fully reversible.

The potentiodynamic response of $Mg(AlCl_2BuEt)_2$ in THF solution is given in FIG. 1b. The electrochemical window spans over 2.3 V, with a magnesium deposition peak starting at −0.3 V (vs.$Mg/Mg^+$) with subsequent magnesium redissolution peak occurring at 0.4 V. As in the previous case, it is evident from the cyclic voltammogram that the process of magnesium deposition and dissolution is fully reversible.

The above-mentioned results compare favorably with the results obtained with the electrolytes suggested by U.S. Pat. No. 4,894,302 to Hoffman et al. The electrochemical window obtained with the prior art organo-borane salts, measured in a comparative study using magnesium dibutyl-diphenyl boronate $(Mg(BBu_2Ph_2)_2)$, spans only about 1.8–1.9 V. The wider electrochemical window obtained using electrolytes according to the present invention indicates improved stability for the electrolytic solution and allows the use of more energetic cathode materials, such that both the cycle life and the energy density of the battery are substantially increased.

The SEM micrographs provided in FIG. 2 show different types of magnesium deposition patterns for electrolytes and electrochemical cells according to the present invention. FIGS. 2a–2b correspond to the electrochemical cell, described above, in which the electrolyte is $Mg(AlCl_3Bu)_2$ in THF solution; FIGS. 2c–2d correspond to the electrochemical cell, described above, in which the electrolyte is $Mg(AlCl_2BuEt)_2$ in THF solution. With $Mg(AlCl_3Bu)_2$, a wider electrochemical window is obtained relative to $Mg(AlCl_2BuEt)_2$. However, the magnesium is deposited as spheres or as spherical clusters. In the case of the $Mg(AlCl_2BuEt)_2$, the salt provides an electrochemical window that is somewhat more narrow, but the magnesium metal deposition is considerably more homogeneous, such that cyclability is greatly enhanced. Both electrolytes display superior electrochemical properties relative to electrolytes according to prior art.

In conjunction with the SEM microscopy, elemental analysis was performed by EDAX (energy dispersive analysis by x-ray fluorescence). The elemental analysis confirmed that the deposition of magnesium metal was substantially pure.

EXAMPLE 3

An electrochemical cell was prepared consisting of a Chevrel-phase cathode, a magnesium metal anode, and an electrolyte containing $Mg(AlCl_2BuEt)_2$ salt in THF. The 25.7 mg cathode was made from a mixture of copper-leached Chevrel-phase material containing 10 weight-% carbon black and 10 weight-% PVDF as a binder, spread on stainless steel mesh. The solution was prepared from 0.25 Molar Mg(AlCl2BuEt)2 salt in THF. The anode was a disc of pure magnesium metal, with a diameter of 16 mm and a thickness of 0.2 mm. The battery was encased in a stainless steel "coin cell" configuration with a paper separator made from glass fibers. The cell was cycled on a standard charger-discharger with a current density of 23.3 milliamperes/gram. The potential limits for the cycling were between 0.5 V at the fully discharged state and 1.8 V for the fully charged state.

The battery was subjected to continuous cycling over 3 months. The excellent cyclability of the battery is clearly evident from FIG. 3, in which the cycles 340–345 are plotted next to the first five cycles (cycles 1–5). The battery performance remains strong over the entire length of the experiment. The charge density obtained in each discharge is 61 ma per gram of the cathode material.

EXAMPLE 4

An electrolyte according to the present invention was prepared as follows: commercial, reagent-grade $MgBu_2$, was dissolved in heptane. Commercial, reagent-grade $AlEtCl_2$ was added drop wise to the $MgBu_2$ solution according to the molar ratio. The mixture was stirred for 48 hours under an inert gas, and $Mg(Bu_2AlCl_2)_3$ was crystallized out of solution. The solvent was removed by evacuation. Ether solvents were added very slowly to the organomagnesium salt to produce a saturated solution (around 0.5M).

The ionic conductivity of the saturated $Mg(Bu_2AlCl_2)_3$ solution was $6.9*10^{-3}$ $Scm^{-1}mol^{-1}$ at 100 kHz in a parallel cell configuration.

It will be appreciated that the above descriptions are intended only to serve as examples, and that many other embodiments are possible within the spirit and the scope of the present invention.

What is claimed is:

1. A non-aqueous electrolyte for use in an electrochemical cell, the electrolyte comprising:
   (a) at least one organic solvent, and
   (b) at least one electrolytically active salt represented by the formula:

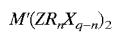

in which:
   M' is selected from the group consisting of magnesium and calcium;
   Z is selected from the group consisting of aluminum and boron;
   R represents radicals independently selected from the following groups: alkyl, alkenyl, aryl, phenyl, benzyl, and amido;

X is a halogen (I, Br, Cl, F);
n=0–3, and
q=4.

2. The non-aqueous electrolyte of claim 1, wherein Z is aluminum.

3. The non-aqueous electrolyte of claim 2, wherein M' is magnesium.

4. The non-aqueous electrolyte of claim 2, wherein M' is calcium.

5. The non-aqueous electrolyte of claim 1, wherein said electrolytically active salt is $Mg[butylAlCl_3]_2$.

6. The non-aqueous electrolyte of claim 1, wherein said electrolytically active salt is $Mg[butylethylAlCl_2]_2$.

7. An electrochemical cell comprising:
   (a) a non-aqueous electrolyte including:
      (i) at least one organic solvent, and
      (ii) at least one electrolytically active salt represented by the formula:

$$M'(ZR'_a R_{n-a} X_{q-n})_2$$

in which:
      M' is selected from the group consisting of magnesium and calcium;
      Z is selected from the group consisting of aluminum and boron;
      R represents radicals selected from the following groups: alkyl, alkenyl, aryl, phenyl, benzyl, and amido;
      R' represents radicals selected from the following groups: alkyl, alkenyl, aryl, phenyl, benzyl, and amido;
      X is a halogen (I, Br, Cl, F);
      a=0–n;
      n=0–3, and
      q=4.

8. The electrochemical cell of claim 7, wherein M' is magnesium and Z is aluminum.

9. The electrochemical cell of claim 7, wherein R and R' are different radicals.

10. The electrochemical cell of claim 7, further comprising:
    (b) a metal anode, and
    (c) an intercalation cathode.

11. The electrochemical cell of claim 7, wherein M' is magnesium, Z is aluminum, and R and R' are alkyl radicals.

12. The electrochemical cell of claim 7, wherein M' is calcium, Z is aluminum, and R and R' are alkyl radicals.

13. The electrochemical cell of claim 7, wherein said organic solvent contains tetrahydrofuran (THF).

14. The electrochemical cell of claim 10, wherein said intercalation cathode is a Chevrel-phase intercalation cathode.

15. The electrochemical cell of claim 11, wherein said Chevrel-phase intercalation cathode is represented by the formula:

$$Cu_x Mg_y Mo_6 S_8$$

wherein x=0–1 and y=0–2.

16. The electrochemical cell of claim 10, wherein said metal anode is magnesium.

17. The electrochemical cell of claim 10, wherein said metal anode is lithium.

18. The electrochemical cell of claim 10, wherein said electrolytically active salt is $Mg[butylAlCl_3]_2$.

19. The electrochemical cell of claim 10, wherein said electrolytically active salt is $Mg[butylethylAlCl_2]_2$.

* * * * *